United States Patent [19]

Leonhard et al.

[11] Patent Number: 5,262,205
[45] Date of Patent: Nov. 16, 1993

[54] PROCESS FOR PRODUCING THE ION-SENSITIVE PROBE ELECTRODE OF A HEAVY-METAL-ION SENSOR

[75] Inventors: Volker Leonhard, Frankfurt am Main; Hartmut Erdmann, Steinbach; Wing F. Chu, Frankfurt am Main, all of Fed. Rep. of Germany

[73] Assignee: Battelle-Institut e.V., Frankfurt, Fed. Rep. of Germany

[21] Appl. No.: 886,229

[22] Filed: May 20, 1992

[30] Foreign Application Priority Data

Jul. 20, 1990 [DE] Fed. Rep. of Germany ....... 4023130
Apr. 18, 1991 [WO] PCT Int'l Appl. ............... PCT/EP91/01346

[51] Int. Cl.⁵ .................... G05D 1/36; B05D 5/12
[52] U.S. Cl. .................... 427/419.7; 427/125; 427/126.1; 427/286; 204/416
[58] Field of Search ........... 427/126.1, 125, 419.7, 427/115, 286; 204/419, 416

[56] References Cited

U.S. PATENT DOCUMENTS 3,892,833  7/1975  Hattori et al. ................. 264/115
4,400,243  8/1983  Ebdon et al. ................. 204/419

FOREIGN PATENT DOCUMENTS 0126452 11/1984 European Pat. Off. .
0366795  5/1990 European Pat. Off. .
2356719  6/1974 Fed. Rep. of Germany .
3639312  5/1988 Fed. Rep. of Germany .
3639802  5/1988 Fed. Rep. of Germany .
3734634  5/1989 Fed. Rep. of Germany .
2102963  2/1983 United Kingdom .

Primary Examiner—Shrive Beck
Assistant Examiner—David M. Maiorana
Attorney, Agent, or Firm—Spencer, Frank & Schneider

[57] ABSTRACT

A method of producing an ion sensitive working electrode for a heavy metal ion sensor, the ion sensitive working electrode including a mixture of $Ag_2S$ and MeS in which Me represents a heavy metal to be determined in a solution to be measured, the method including applying a conductive layer onto a substrate using at least one thick-film technique selected from the group consisting essentially of screen printing and film casting; applying a layer comprised of a plurality of juxtaposed sections on top of the conductive layer, each section of the plurality of juxtaposed sections being comprised of a mixture of $Ag_2S$ and MeS, with each section of the plurality of juxtaposed sections containing a different heavy metal, Me; and applying a covering layer on top of the layer comprised of a plurality of juxtaposed sections and on top of at least a portion of the conductive layer, which portion of the conductive layer will contact the solution to be measured in use whereby the covering layer protects the conductive layer from the solution to be measured in use, the covering layer having defined therein a plurality of window regions, one window region for each section of the plurality of juxtaposed sections, whereby the solution to be measured in use is provided access to the layer comprised of a plurality of juxtaposed sections.

3 Claims, 1 Drawing Sheet

PROCESS FOR PRODUCING THE ION-SENSITIVE PROBE ELECTRODE OF A HEAVY-METAL-ION SENSOR

CROSS REFERENCE TO RELATED APPLICATION

This application is a continuing application of copending application PCT/EP91/01346 filed Jul. 18th, 1991 which claims the priority of German Application P 4023130.5 filed Jul. 20th, 1990, the rights of priority of which are also claimed for the present application. Both applications are incorporated herein by reference.

BACKGROUND OF THE INVENTION

1. Field of the Invention

The present invention relates to a method of producing an ion sensitive working electrode for a heavy metal ion sensor. The electrode includes a mixture of $Ag_2S$ and Mes, with Me being the heavy metal to be determined.

2. Background of the Related Art

Together with a measuring solution containing the heavy metal ions to be determined and with a reference electrode, preferably an Ag/AgCl reference electrode, the mentioned working electrode constitutes a heavy metal ion sensor. The principle of such sensors is described, for example, in the book by Cammann, entitled "Das Arbeiten mit ionensensitiven Elektroden" [Working With Ion Sensitive Electrodes], published by Springer-Verlag, Berlin, Heidelberg, New York, 1977, particularly pages 59–66. Such conventional working electrodes are relatively large. They also break easily because a glass tube is employed as the casing. A particular drawback is that they are relatively expensive to manufacture (approximately DM 200.00 to 800.00 retail price each). Moreover, only a single heavy metal can be detected with the prior art sensor.

DE-OS 3,639,312 corresponding to U.S. Pat. No. 4,908,118 discloses a solid state electrode for the determination of sodium concentrations in solutions; this electrode is produced in thick-film technology. The various layers are here applied on top of one another and next to one another onto a substrate to form together the solid state electrode. If necessary, the layers are provided with a cover which exposes and permits access to the solid state electrolyte membrane provided there. However, with this prior art solid state electrode it is not possible to detect heavy metal ions. And again only a single material can be detected, namely the concentration of sodium ions in solutions.

Similar prior art is disclosed in DE-OS 3,639,802 which discloses a sensor produced in thick film technology for monitoring the hydrogen concentrations in gases.

Additionally, reference is also made to British Patent 2,102,963-A which discloses several embodiments of an ion selective electrode in the form of a film, with the electrode including a conductive layer and an ion selective layer laminated thereon so as to cover at least one edge of the conductive layer.

Based on a method including the above-mentioned features, it is therefore an object of the present invention, to develop this method in such a way that an economical manufacture results in a working electrode whose sensor is able to detect different heavy metals. The sensor should be easily miniaturized and easily manipulated; in particular, it should not be fragile.

SUMMARY OF THE INVENTION

To solve this problem, the present invention is characterized in that a plurality of juxtaposed conductive layers are applied to a substrate using thick-film technology and, on top of that, a plurality of layers of a mixture of $Ag_2S$ and MeS, which differ from one another by their different heavy metals Me; on top of that again a covering layer which protects the conductive layer against a measuring solution that contains the heavy metal ions to be determined and gives the measuring solution access to the mixed layer of $Ag_2S$/MeS.

With these measures, a heavy metal sensor having a homogeneous solid state membrane electrode based on $Ag_2S$ is produced using thick-film technology and permits a potentiometric determination of the concentration or activity of heavy metal ions in solutions.

In contrast to GB 2,102,964-A, the ion selective layer, the $Ag_2S$/MeS mixture, is applied as a mixture, and there is no longer any chemical or electrochemical modification.

Due to the use of thick-film technology, no glass casing is required since non-breakable materials, preferably plastic, can be employed for the covering layer.

Thick film technology permits economical manufacture of the working electrodes and of correspondingly completed sensors, with it only being necessary to take care, upon application of the mixed layer that the layer contains the different metals to be determined next to one another and separated from one another. All this can be manufactured very easily and in a very labor saving manner in the thick-film process employed.

Although DE 3,734,634.A1 discloses the juxtaposition of sensitive and selective regions in suspended gate field effect transistors, the latter are produced in a completely different manner, namely, by fully automatic potentiostatic or galvanostatic deposition. These process measures, on the one hand, cannot be employed in connection with the above-mentioned different arrangements that are to be produced using thick-film technology; on the other hand, they would lead to Ag-/$Ag_2S$/MeS arrangements which would not have the required characteristics of good layer adhesion and impermeability of the cover layers.

An Ag layer is preferred for the conductive layer.

The term thick-film technology includes screen-printing or film casting, as well as combinations of both techniques.

BRIEF DESCRIPTION OF THE DRAWINGS

The invention will now be described in greater detail with reference to the accompanying drawing wherein.

DESCRIPTION OF THE PREFERRED EMBODIMENTS

Figure 1:
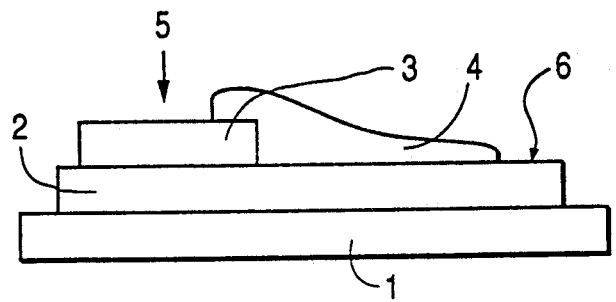
FIG. 1 is a schematic sectional view of a working electrode according to the invention.

FIG. 1 depicts a substrate 1 onto which an Ag layer 2 is printed. On top of that, a layer 3 composed of a mixture of $Ag_2S$ and MeS is applied in thick-film technology, with Me representing the heavy metal to be determined.

A cover layer 4 covers conductive layer 2 at least in the region in which the sensor dips into a measuring solution. This protects the Ag layer 2 against the measuring solution. The cover layer 4 of glass and plastic leaves open a window in region 5 through which the measuring solution has access to layer 3.

FIG. 1 also shows a connecting lead 6 by means of which the potential can be picked up.

Figure 2:
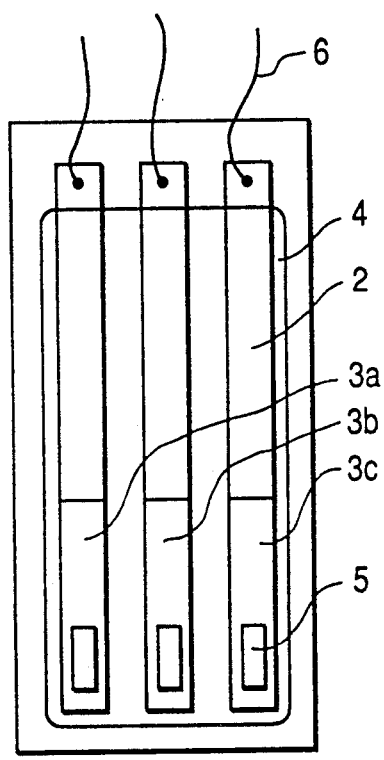
FIG. 2 is a top view of the working electrode of FIG. 1.

FIG. 2 shows that, if the structure shown in principle in FIG. 1 is maintained, several mixture layers 3 are applied separately from one another onto the Ag layer 2, namely, mixture layers 3a, 3b and 3c. These layers differ from one another by the different metals their mixtures contain. If one dips the sensor - completed by a reference electrode - into a measuring solution, the heavy metal ions of the metals contained in mixed layers 3a, 3b and 3c are determined and also the concentration of the respective heavy metal ions.

In addition to the $MeS/Ag_2S$ electrodes, other combinations are also of significance, specifically for anions:
- $AgI/Ag_2S$ as an ion selective electrode for a determination of iodide ions;
- $AgBr/Ag_2S$ for a determination of bromide ions.

Figure 3:
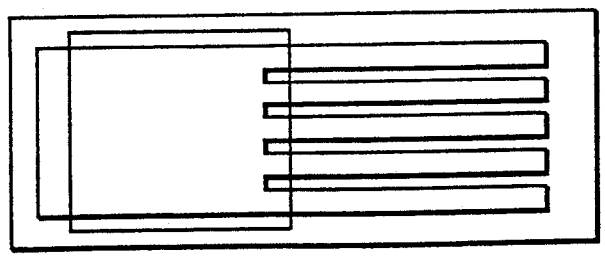
FIG. 3 is a top view showing a modified electrode.

An arrangement as shown in the FIG. 3, greatly increases the number of contact regions between measuring solution and electrode, resulting in an improved response behavior.

Obviously, numerous and additional modifications and variations of the present invention are possible in light of the above teachings. It is therefore to be understood that within the scope of the appended claims, the invention may be practiced otherwise than as specifically claimed.

What is claimed is:

1. A method of producing an ion sensitive working electrode for a heavy metal ion sensor, the ion sensitive working electrode including a mixture of $Ag_2S$ and MeS in which Me represents a heavy metal to be determined in a solution to be measured, the method comprising:
   a. applying a conductive layer onto a substrate using at least one thick-film technique selected from the group consisting essentially of screen printing and film casting;
   b. applying a layer comprised of a plurality of juxtaposed sections on top of the conductive layer, each section of the plurality of juxtaposed sections being comprised of a mixture of $Ag_2S$ and MeS, with each section of the plurality of juxtaposed sections containing a different heavy metal, Me; and
   c. applying a covering layer on top of the layer comprised of a plurality of juxtaposed sections and on top of at least a portion of the conductive layer, which portion of the conductive layer will contact the solution to be measured in use whereby the covering layer protects the conductive layer from the solution to be measured in use, the covering layer having defined therein a plurality of window regions, one window region for each section of the plurality of juxtaposed sections, whereby the solution to be measured in use is provided access to the layer comprised of a plurality of juxtaposed sections.

2. The method as defined in claim 1, wherein the conductive layer is an Ag layer.

3. The method as defined in claim 1, wherein the heavy metal in the mixture is selected from the group consisting of Pb, Cu, and Cd.

* * * * *